US006806065B2

(12) United States Patent
Bouyer et al.

(10) Patent No.: US 6,806,065 B2
(45) Date of Patent: Oct. 19, 2004

(54) ***RICKETTSIA FELIS* OUTER MEMBRANE PROTEIN**

(75) Inventors: Donald H. Bouyer, Galveston, TX (US); Patricia Crocquet-Valdes, Galveston, TX (US); John Stenos, Highton (AU); David H. Walker, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 09/800,065

(22) Filed: Mar. 6, 2001

(65) Prior Publication Data

US 2002/0094552 A1 Jul. 18, 2002

Related U.S. Application Data

(60) Provisional application No. 60/187,323, filed on Mar. 6, 2000.

(51) Int. Cl.$^7$ .............................................. C12N 15/09
(52) U.S. Cl. .................. 435/69.3; 536/23.7; 435/320.1; 435/69.1; 435/69.7; 435/243; 435/252.3; 435/325; 435/348; 435/6
(58) Field of Search ........................... 424/234.1, 265.1; 536/23.1, 23.7; 435/320.1, 69.1, 69.3, 69.7, 243, 252.3, 325, 348, 6

(56) References Cited

U.S. PATENT DOCUMENTS 5,952,194 A * 9/1999 Stiegler

OTHER PUBLICATIONS

Bouyer et al, The Identification and Characterization of a Previously Undiscovered rOMPA Encoding Gene in Rickettsia Felis, 1999Annual McLaughlin Fellowship Colloquium(Mar. 1999)(abstract).
Bouyer et al, The Identification and Characterization of a Previously Undiscovered rOMPA Encoding Gene in Rickettsia Felis, inRickettsia and Rickettsial Diseases at the Turn of the Third Millennium, (Jun. 1999)(abstract).
Bouyer et al., The Identification and Characterization of A Previously Undiscovered rOMPA Encoding Gene in Rickettsia Felis, In Rickettsiae and Rickettsial Diseases at the Turn of the Third Millennium, pp. 11–15 edited by D. Rauolt & P. Brouqui, Paris France (Jun. 1999).

Zavala–Velasquez et al., Rickettsia felis Rickettslosis in Yucatan, THE LANCET, 356:1079–80(2000).

Bouyer et al., Rickettsia felis:Molecular Characterization of a New Member of the Spotted Fever Group, Intl J Systematic & Evolutionary Micro, 51:338–347(2001).

Moron et al., Phylogenetic Analysis of the rompB Genes of Rickettsia Felis and Rickettsia Prowazekii European–Human and North American Flying–Squirrel Strains, Am. J. Trop. Med. Hyg., 62(5)(2000).

Williams et al., Typhus and Typhuslike Rickettsiae Associated with Opossums and Their Fleas in Los Angeles County, California, J. Clinical Micro, 30(7):1758–62(1992).

Schriefer et al., Identification of a Novel Rickettsial Infection in a Patient Diagnosed with Murine Typhus, J. Clin. Micro. 32(4):949–54(1994).

Zavala–Velasquez, Unrecognized Spotted Fever Group Rickettsiosis Masquerading As Dengue Fever in Mexico, Am. J. Trop. Med. Hyg., 55(2):157–59(1996).

Schriefer et al., Murine Typhus:Updated Roles of Multiple Urban Components and a Second Typhuslike Rickettsia, J. Med. Entomology, 31(5):681–5(1994).

* cited by examiner

Primary Examiner—Jennifer E. Graser
(74) Attorney, Agent, or Firm—Rogalsky & Weyand, LLP

(57) ABSTRACT

The present invention is directed to isolated nucleic acid molecules encoding *Rickettsia felis* outer membrane proteins (*R. felis* omp). Expression vectors and host cells comprising the nucleic acid molecules are also provided, as well as methods for increasing or decreasing the expression of *R. felis* omp in host cells. The invention further provides a method of screening a substance for the ability of the substance to modify *R. felis* omp function, and a method for isolating other *R. felis* omp molecules. DNA oligomers capable of hybridizing to the nucleic acid molecule encoding the *R. felis* omp are provided, which can be used to detect *R. felis* omp in a sample. An isolated *R. felis* omp is also provided. Antibodies specific for the protein, and fragments thereof, are provided, as are compositions comprising the protein and a compatible carrier. The subject invention further provides a method of preventing *R. felis* infections by *R. felis* present in a carrier host, and a method of reducing *R. felis* infection of a carrier host.

16 Claims, No Drawings

RICKETTSIA FELIS OUTER MEMBRANE PROTEIN

This application claims priority of U.S. Provisional Patent Application No. 60/187,323, filed Mar. 6, 2000.

The subject matter of this application was made with support from the United States Government under National Institutes of Health, NIAID, Grant Nos. AI21242 and AI31431 and the National Institutes of Health Grant No. D43 TW00903.

The U.S. Government may have certain rights in this invention.

FIELD OF THE INVENTION

The present invention relates generally to a *Rickettsia* protein, and more particularly to *Rickettsia felis* outer membrane protein and uses thereof.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

In 1990, during a study investigating potential vectors for *Ehrlichia risticii*, rickettsia-like organisms were observed in the midgut epithelial cells of adult cat fleas, *Ctenocephalides felis*, by electron microscopy (Adams et al., 1990). The organisms were found only in a group of fleas obtained from El Labs, from which the original designation of the organism (ELB) was derived, and not in any of the other three sources of fleas. The organisms were described as having an ultrastructure and infection pattern similar to that of *R. typhi*. The organisms were 0.25–0.45 μm in diameter by 1.5 μm in length and were found not only in the midgut, but also in the tracheal matrix, muscles and reproductive tissues of the fleas. The organisms contained trilaminar cell walls that were characteristic of rickettsiae with a well-defined inner cell membrane and outer membrane. Measurements of the microcapsular layer, outer and inner leaflets of the outer membrane, and the periplasmic space strongly resembled other Rickettsia species.

The first attempts to characterize the organism involved the amplification of the 17-kDa antigen, citrate synthase (CS) and 190 kDa antigen (rompA) genes (Azad et al., 1992). The ELB agent was found to be distinguishable from *R. typhi* by restriction fragment length polymorphism (RFLP) analysis of the 17-kDa gene product digested with Aha II or Alu I. The CS gene was used to confirm that the organism found in the cat fleas was the ELB agent and not *R. typhi*, which can also be found occasionally in these fleas. The RFLP pattern of the CS gene amplified from the ELB agent in cat fleas differed from that of *R. typhi*. Attempts at that time to amplify the rompA gene from the ELB agent proved to be unsuccessful.

This study also provided evidence that the ELB agent can be transmitted transstadially and transovarially by two experimental observations. Unfed cat fleas that were negative by polymerase chain reaction (PCR) for the ELB agent tested positive for the 17-kDa protein gene of the ELB agent after feeding on infected cats (Azad et al., 1992). Also the ELB agent was present in freshly deposited eggs as determined by PCR (Azad et al., 1992).

The first serologic assays for the ELB agent were also conducted in this study. Antisera and monoclonal antibodies generated against *R. typhi* were used to examine smears of newly emerged fleas from both the El Labs and negative controls. Indirect immunofluorescent staining detected the ELB agent in the sample fleas, but not in the control fleas. In surveys of fleas in Los Angeles County, Calif. and in Texas, the 17-kDa and CS genes were used to investigate the natural occurrence of the ELB agent (Williams et al., 1992; Schriefer et al., 1994a). The results from both studies indicated that infection of the cat flea with the ELB agent is more prevalent than *R. typhi*. One study reported an infection rate of 3.8% for the ELB agent (Schriefer et al., 1994a).

The ELB agent has been identified in flea colonies from various regions of the United States through the use of RFLP analysis of PCR products of the 17-kDa and CS genes (Higgins et al., 1996). Analysis of the eight colonies showed that the colonies were infected with the ELB agent with a range of prevalence within each colony of 43 to 93%. The possible source of ELB in these colonies was subsequently traced to the El Labs, which provided fleas as starter stock or to replenish the colony. Attempts to infect mammalian cells and SCID mice with the ELB agent were not successful. Two publications are based upon the study of organisms considered to represent ELB agent propagated in cell culture (Radulovic et al., 1995a; Radulovic et al., 1995b); however, the cultured agent could not be reproducibility propagated and maintained in further culture.

In 1996, it was proposed that the ELB agent be designated as *Rickettsia felis* in recognition of its discovery and origin in the cat flea (Higgins et al., 1996). Subsequent additions to the knowledge of *R. felis* have used this name in the biomedical and scientific literature (Noden et al., 1998, Andersson & Andersson, 1999, Andersson et al., 1999, Bouyer et al., 1999).

There have been reports implicating the involvement of *R. felis* in human disease indicating its potential importance as a newly emerging pathogen. (Schriefer et al., 1994a). Given the evidence that infectious diseases are transmitted by *Ctenocephalides felis* cat fleas via *Rickettsia felis*, identification of *R. felis* proteins can lead to methods for interfering with/preventing *R. felis* infections based on knowledge of those *R. felis* proteins.

SUMMARY OF THE INVENTION

To this end, DNA from cat fleas naturally infected with *R. felis* was amplified by polymerase chain reaction utilizing primer sets specific for the 190-kDa surface antigen (rOmpA) and 17-kDa antigen genes. The entire 5513 base pair rompA gene was sequenced, characterized and found to have several unique features when compared to the rompA genes of other *Rickettsia*. Phylogenetic analysis of the partial sequence of the 17-kDa antigen gene indicates that *R. felis* is less divergent from the spotted fever group (SFG) rickettsiae than from the typhus group rickettsiae. The organism is passed transstadially and transovarially, and infection in the cat flea has been observed in the midgut, tracheal matrix, muscle, hypodermis, ovaries, and testes.

The subject invention provides an isolated nucleic acid molecule encoding a *Rickettsia felis* outer membrane protein. The invention also provides an antisense nucleic acid molecule complementary to at least a portion of the mRNA encoding the *Rickettsia felis* outer membrane protein.

The isolated nucleic acid molecules of the invention can be inserted into suitable expression vectors and/or host cells. Expression of the nucleic acid molecules encoding the *Rickettsia felis* outer membrane protein results in production of *Rickettsia felis* outer membrane protein in a host cell.

Expression of the antisense nucleic acid molecules in a host cell results in decreased expression of the *Rickettsia felis* outer membrane protein.

The invention further provides a ribozyme having a recognition sequence complementary to a portion of mRNA encoding a *Rickettsia felis* outer membrane protein. The ribozyme can be introduced into a cell to also achieve decreased expression of *Rickettsia felis* outer membrane protein in the cell.

The invention further provides a method of screening a substance for the ability of the substance to modify *Rickettsia felis* outer membrane protein function, and a method of obtaining DNA encoding a *Rickettsia felis* outer membrane protein.

Further provided is an isolated nucleic acid molecule encoding a *Rickettsia felis* outer membrane protein, wherein the nucleic acid molecule encodes a first amino acid sequence having at least 90% amino acid identity to a second amino acid sequence. The second amino acid sequence is as shown in SEQ ID NO:2.

The invention further provides a DNA oligomer capable of hybridizing to a nucleic acid molecule encoding a *Rickettsia felis* outer membrane protein. The DNA oligomer can be used in a method of detecting presence of a *Rickettsia felis* outer membrane protein in a sample, which method is also provided by the subject invention.

The invention also provides an isolated *Rickettsia felis* outer membrane protein, and antibodies or antibody fragments specific for the *Rickettsia felis* outer membrane protein. The antibodies and antibody fragments can be used to detect the presence of the *Rickettsia felis* outer membrane protein in samples. Further provided is an isolated *Rickettsia felis* outer membrane protein encoded by a first amino acid sequence having at least 90% amino acid identity to a second amino acid sequence, the second amino acid sequence as shown in SEQ ID NO:2.

The subject invention further provides a method of preventing *Rickettsia felis* infections by *Rickettsia felis* present in a carrier host, the method comprising administering to the carrier host an amount of a compound effective to modify levels of functional *Rickettsia felis* outer membrane protein in *Rickettsia felis* present in the carrier host.

The invention also provides a method of reducing *Rickettsia felis* infection of a carrier host, the method comprising administering to the carrier host an amount of a compound effective to prevent function of a *Rickettsia felis* outer membrane protein in the carrier host.

DETAILED DESCRIPTION OF THE INVENTION

The term "nucleic acid", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA, and nonfunctional DNA or RNA.

"Isolated" nucleic acid refers to nucleic acid which has been separated from an organism in a substantially purified form (i.e. substantially free of other substances originating from that organism), and to synthetic nucleic acid.

By a nucleic acid sequence "homologous to" or "complementary to", it is meant a nucleic acid that selectively hybridizes, duplexes or binds to DNA sequences encoding the protein or portions thereof when the DNA sequences encoding the protein are present in a genomic or cDNA library. A DNA sequence which is similar or complementary to a target sequence can include sequences which are shorter or longer than the target sequence so long as they meet the functional test set forth.

Typically, the hybridization is done in a Southern blot protocol using a 0.2×SSC, 0.1% SDS, 65° C. wash. The term "SSC" refers to a citrate-saline solution of 0.15M sodium chloride and 20 mM sodium citrate. Solutions are often expressed as multiples or fractions of this concentration. For example, 6×SSC refers to a solution having a sodium chloride and sodium citrate concentration of 6 times this amount or 0.9 M sodium chloride and 120 mM sodium citrate. 0.2×SSC refers to a solution 0.2 times the SSC concentration or 0.03M sodium chloride and 4 mM sodium citrate.

The phrase "nucleic acid molecule encoding" refers to a nucleic acid molecule which directs the expression of a specific protein or peptide. The nucleic acid sequences include both the DNA strand sequence that is transcribed into RNA and the RNA sequence that is translated into protein or peptide. The nucleic acid molecule includes both the full length nucleic acid sequences as well as non-full length sequences derived from the full length protein. It being further understood that the sequence includes the degenerate codons of the native sequence or sequences which may be introduced to provide codon preference in a specific host cell.

The term "located upstream" as used herein refers to linkage of a promoter upstream from a nucleic acid (DNA) sequence such that the promoter mediates transcription of the nucleic acid (DNA) sequence.

The term "vector", refers to viral expression systems, autonomous self-replicating circular DNA (plasmids), and includes both expression and nonexpression plasmids. Where a recombinant microorganism or cell is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or the vector may be incorporated within the host's genome.

The term "plasmid" refers to an autonomous circular DNA molecule capable of replication in a cell, and includes both the expression and nonexpression types. Where a recombinant microorganism or cell is described as hosting an "expression plasmid", this includes latent viral DNA integrated into the host chromosome(s). Where a plasmid is being maintained by a host cell, the plasmid is either being stably replicated by the cell during mitosis as an autonomous structure, or the plasmid is incorporated within the host's genome.

The phrase "heterologous protein" or "recombinantly produced heterologous protein" refers to a peptide or protein of interest produced using cells that do not have an endogenous copy of DNA able to express the peptide or protein of interest. The cells produce the peptide or protein because they have been genetically altered by the introduction of the appropriate nucleic acid sequences. The recombinant peptide or protein will not be found in association with peptides or proteins and other subcellular components normally associated with the cells producing the peptide or protein.

The following terms are used to describe the sequence relationships between two or more nucleic acid molecules or polynucleotides, or between two or more amino acid sequences of peptides or proteins: "reference sequence", "comparison window", "sequence identity", "sequence homology", "percentage of sequence identity", "percentage of sequence homology", "substantial identity", and "substantial homology". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted, for example, by the local homology algorithm of Smith and Waterman (1981), by the homology alignment algorithm of Needleman and Wunsch (1970), by the search for similarity method of Pearson and Lipman (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to nucleic acid molecules or polynucleotides, the terms "substantial identity" or "substantial sequence identity" mean that two nucleic acid sequences, when optimally aligned (see above), share at least 90 percent sequence identity, preferably at least 95 percent sequence identity, more preferably at least 96, 97, 98 or 99 percent sequence identity.

"Percentage nucleotide (or nucleic acid) identity" or "percentage nucleotide (or nucleic acid) sequence identity" refers to a comparison of the nucleotides of two nucleic acid molecules which, when optimally aligned, have approximately the designated percentage of the same nucleotides. For example, "95% nucleotide identity" refers to a comparison of the nucleotides of two nucleic acid molecules which when optimally aligned have 95% nucleotide identity. Preferably, nucleotide positions which are not identical differ by redundant nucleotide substitutions (the nucleotide substitution does not change the amino acid encoded by the particular codon).

As further applied to nucleic acid molecules or polynucleotides, the terms "substantial homology" or "substantial sequence homology" mean that two nucleic acid sequences, when optimally aligned (see above), share at least 90 percent sequence homology, preferably at least 95 percent sequence homology, more preferably at least 96, 97, 98 or 99 percent sequence homology.

"Percentage nucleotide (or nucleic acid) homology" or "percentage nucleotide (or nucleic acid) sequence homology" refers to a comparison of the nucleotides of two nucleic acid molecules which, when optimally aligned, have approximately the designated percentage of the same nucleotides or nucleotides which are not identical but differ by redundant nucleotide substitutions (the nucleotide substitution does not change the amino acid encoded by the particular codon). For example, "95% nucleotide homology" refers to a comparison of the nucleotides of two nucleic acid molecules which when optimally aligned have 95% nucleotide homology.

As applied to polypeptides, the terms "substantial identity" or "substantial sequence identity" mean that two peptide sequences, when optimally aligned, such as by the programs GAP or BESTFIT using default gap, share at least 90 percent sequence identity, preferably at least 95 percent sequence identity, more preferably at least 96, 97, 98 or 99 percent sequence identity.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to affect the properties of a protein. Examples include glutamine for asparagine or glutamic acid for aspartic acid.

As further applied to polypeptides, the terms "substantial homology" or "substantial sequence homology" mean that two peptide sequences, when optimally aligned, such as by the programs GAP or BESTFIT using default gap, share at least 90 percent sequence homology, preferably at least 95 percent sequence homology, more preferably at least 96, 97, 98 or 99 percent sequence homology.

"Percentage amino acid homology" or "percentage amino acid sequence homology" refers to a comparison of the amino acids of two polypeptides which, when optimally aligned, have approximately the designated percentage of the same amino acids or conservatively substituted amino acids. For example, "95% amino acid homology" refers to a comparison of the amino acids of two polypeptides which when optimally aligned have 95% amino acid homology. As used herein, homology refers to identical amino acids or residue positions which are not identical but differ only by conservative amino acid substitutions. For example, the substitution of amino acids having similar chemical properties such as charge or polarity are not likely to affect the properties of a protein. Examples include glutamine for asparagine or glutamic acid for aspartic acid.

The phrase "substantially purified" or "isolated" when referring to a protein (or peptide), means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein (or peptide) which is the predominant species present in a preparation is substantially purified. Generally, a substantially purified or isolated protein (or peptide) will comprise more than 80% of all macromolecular species present in the preparation. Preferably, the protein (or peptide) is purified to represent greater than 90% of all macromolecular species present. More preferably the protein (or peptide) is purified to greater than 95%, and most preferably the protein (or peptide) is purified to essential homogeneity, wherein other macromolecular species are not detected by conventional techniques. A "substantially purified" or "isolated" protein (or peptide) can be separated from an organism, synthetically or chemically produced, or recombinantly produced.

"Biological sample" or "sample" as used herein refers to any sample obtained from a living organism or from an organism that has died. Examples of biological samples include body fluids and tissue specimens.

High stringent hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, i.e. salt or formamide concentration, and the extent of base mismatching, the combination of parameters is more important than the absolute measure of any one. High stringency may be attained, for example, by overnight hybridization at about 68° C. in a 6×SSC solution, washing at room temperature with 6×SSC solution, followed by washing at about 68° C. in a 6×SSC solution then in a 0.6×SSX solution.

Hybridization with moderate stringency may be attained, for example, by: 1) filter pre-hybridizing and hybridizing with a solution of 3×sodium chloride, sodium citrate (SSC), 50% formamide, 0.1M Tris buffer at pH 7.5, 5×Denhardt's solution; 2) pre-hybridization at 37° C. for 4 hours; 3) hybridization at 37° C. with amount of labeled probe equal to 3,000,000 cpm total for 16 hours; 4) wash in 2×SSC and 0.1% SDS solution; 5) wash 4× for 1 minute each at room temperature and 4× at 60° C. for 30 minutes each; and 6) dry and expose to film.

The phrase "selectively hybridizing to" refers to a nucleic acid molecule that hybridizes, duplexes or binds only to a particular target DNA or RNA sequence when the target sequences are present in a preparation of total cellular DNA or RNA. By selectively hybridizing it is meant that a nucleic acid molecule binds to a given target in a manner that is detectable in a different manner from non-target sequence under moderate, or more preferably under high, stringency conditions of hybridization. "Complementary" or "target" nucleic acid sequences refer to those nucleic acid sequences which selectively hybridize to a nucleic acid molecule. Proper annealing conditions depend, for example, upon a nucleic acid molecule's length, base composition, and the number of mismatches and their position on the molecule, and must often be determined empirically. For discussions of nucleic acid molecule (probe) design and annealing conditions, see, for example, Sambrook et al. 1989.

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid sequence of the signal peptide or other peptide/protein to which the relevant sequence listing relates.

The DNA molecules of the subject invention also include DNA molecules coding for protein analogs, fragments or derivatives of the protein which differ from naturally-occurring forms (the naturally-occurring protein) in terms of the identity or location of one or more amino acid residues (deletion analogs containing less than all of the residues specified for the protein, substitution analogs wherein one or more residues specified are replaced by other residues, and addition analogs wherein one or more amino acid residues are added to a terminal or medial portion of the protein) and which share the signal property of the naturally-occurring form. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

As used herein, a "peptide" refers to an amino acid sequence of three to one hundred amino acids, and therefore an isolated peptide that comprises an amino acid sequence is not intended to cover amino acid sequences of greater than 100 amino acids. Preferably, the peptides that can be identified and used in accordance with the subject invention (whether they be mimotope or anti-mimotope peptides) are less than 50 amino acids in length, and more preferably the peptides are five to 20 amino acids in length or 20–40 amino acids in length.

The peptides can contain any naturally-occurring or non-naturally-occurring amino acids, including the D-form of the amino acids, amino acid derivatives and amino acid mimics, so long as the desired function and activity of the peptide is maintained. The choice of including an (L)- or a (D)-amino acid in the peptides depends, in part, on the desired characteristics of the peptide. For example, the incorporation of one or more (D)-amino acids can confer increased stability on the peptide and can allow a peptide to remain active in the body for an extended period of time. The incorporation of one or more (D)-amino acids can also increase or decrease the pharmacological activity of the peptide.

The peptides may also be cyclized, since cyclization may provide the peptides with superior properties over their linear counterparts.

As used herein, the terms "amino acid mimic" and "mimetic" mean an amino acid analog or non-amino acid moiety that has the same or similar functional characteristic of a given amino acid. For instance, an amino acid mimic of a hydrophobic amino acid is one which is non-polar and retains hydrophobicity, generally by way of containing an aliphatic chemical group. By way of further example, an arginine mimic can be an analog of arginine which contains a side chain having a positive charge at physiological pH, as is characteristic of the guanidinium side chain reactive group of arginine.

In addition, modifications to the peptide backbone and peptide bonds thereof are also encompassed within the scope of amino acid mimic or mimetic. Such modifications can be made to the amino acid, derivative thereof, non-amino acid moiety or the peptide either before or after the amino acid, derivative thereof or non-amino acid moiety is incorporated into the peptide. What is critical is that such modifications mimic the peptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., JOC, 46:257 (1981) and Raucher et al., Tetrahedron. Lett., 21:14061 (1980). An amino acid mimic is, therefor, an organic molecule that retains the similar amino acid pharmacophore groups as is present in the corresponding amino acid and which exhibits substantially the same spatial arrangement between functional groups.

The substitution of amino acids by non-naturally occurring amino acids and amino acid mimics as described above can enhance the overall activity or properties of an individual peptide based on the modifications to the backbone or side chain functionalities. For example, these types of alterations to the specifically described amino acid substituents and exemplified peptides can enhance the peptide's stability to enzymatic breakdown and increase biological activity. Modifications to the peptide backbone similarly can add stability and enhance activity.

One skilled in the art, using the above sequences or formulae, can easily synthesize the peptides. Standard procedures for preparing synthetic peptides are well known in the art. The novel peptides can be synthesized using: the solid phase peptide synthesis (SPPS) method of Merrifield (J. Am. Chem. Soc., 85:2149 (1964)) or modifications of SPPS; or, the peptides can be synthesized using standard solution methods well known in the art (see, for example, Bodanzsky, M., Principles of Peptide Synthesis, 2nd revised ed., Springer-Verlag (1988 and 1993)). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, Proc. Natl. Acad. Sci., USA 82:5131 (1985).

With these definitions in mind, the subject invention provides an isolated nucleic acid molecule encoding a *Rickettsia felis* outer membrane protein. The nucleic acid molecule can be deoxyribonucleic acid (DNA) or ribonucleic acid (RNA, including messenger RNA or mRNA), genomic or recombinant, biologically isolated or synthetic.

The DNA molecule can be a cDNA molecule, which is a DNA copy of a messenger RNA (mRNA) encoding the channel.

An example of such a *Rickettsia felis* outer membrane protein is the *Rickettsia felis* outer membrane protein encoded by the nucleotide sequence as shown in SEQ ID NO:1 (this is the open reading frame). The amino acid sequence encoded by this nucleotide sequence is shown in SEQ ID NO:2. The nucleotide sequence of the full gene for the *Rickettsia felis* outer membrane protein is shown in SEQ ID NO:3.

The invention also provides an antisense nucleic acid molecule that is complementary to at least a portion of the mRNA encoding the *Rickettsia felis* outer membrane protein. Antisense nucleic acid molecules can be RNA or single-stranded DNA, and can be complementary to the entire mRNA molecule encoding the protein (i.e. of the same nucleotide length as the entire molecule). It may be desirable, however, to work with a shorter molecule. In this instance, the antisense molecule can be complementary to a portion of the entire mRNA molecule encoding the protein. These shorter antisense molecules are capable of hybridizing to the mRNA encoding the entire molecule, and preferably consist of about twenty to about one hundred nucleotides. These antisense molecules can be used to reduce levels of *Rickettsia felis* outer membrane protein, by introducing into cells an RNA or single-stranded DNA molecule that is complementary to at least a portion of the mRNA of the protein (i.e. by introducing an antisense molecule). The antisense molecule can base-pair with the mRNA of the protein, preventing translation of the mRNA into protein. Thus, an antisense molecule to the protein can prevent translation of mRNA encoding the protein into a functional protein. It may be desirable to place the antisense molecule downstream and under the control of a particular promoter, so that the antisense will prevent translation of mRNA encoding the protein only in cells in which the particular promoter functions.

More particularly, an antisense molecule complementary to at least a portion of mRNA encoding a *Rickettsia felis* outer membrane protein can be used to decrease expression of a functional channel. A cell with a first level of expression of a functional *Rickettsia felis* outer membrane protein is selected, and then the antisense molecule is introduced into the cell. The antisense molecule blocks expression of functional *Rickettsia felis* outer membrane protein, resulting in a second level of expression of a functional *Rickettsia felis* outer membrane protein in the cell. The second level is less than the initial first level.

Antisense molecules can be introduced into cells by any suitable means. In one embodiment, the antisense RNA molecule is injected directly into the cellular cytoplasm, where the RNA interferes with translation. A vector may also be used for introduction of the antisense molecule into a cell. Such vectors include various plasmid and viral vectors. For a general discussion of antisense molecules and their use, see Han et al. 1991 and Rossi 1995.

The invention further provides a special category of antisense RNA molecules, known as ribozymes, having recognition sequences complementary to specific regions of the mRNA encoding the *Rickettsia felis* outer membrane protein. Ribozymes not only complex with target sequences via complementary antisense sequences but also catalyze the hydrolysis, or cleavage, of the template mRNA molecule.

Expression of a ribozyme in a cell can inhibit gene expression (such as the expression of a *Rickettsia felis* outer membrane protein). More particularly, a ribozyme having a recognition sequence complementary to a region of a mRNA encoding a *Rickettsia felis* outer membrane protein can be used to decrease expression of *Rickettsia felis* outer membrane protein. A cell with a first level of expression of *Rickettsia felis* outer membrane protein is selected, and then the ribozyme is introduced into the cell. The ribozyme in the cell decreases expression of *Rickettsia felis* outer membrane protein in the cell, because mRNA encoding the *Rickettsia felis* outer membrane protein is cleaved and cannot be translated.

Ribozymes can be introduced into cells by any suitable means. In one embodiment, the ribozyme is injected directly into the cellular cytoplasm, where the ribozyme cleaves the mRNA and thereby interferes with translation. A vector may be used for introduction of the ribozyme into a cell. Such vectors include various plasmid and viral vectors (note that the DNA encoding the ribozyme does not need to be "incorporated" into the genome of the host cell; it could be expressed in a host cell infected by a viral vector, with the vector expressing the ribozyme, for instance). For a general discussion of ribozymes and their use, see Sarver et al. 1990, Chrisey et al. 1991, Rossi et al. 1992, and Christoffersen et al. 1995.

The nucleic acid molecules of the subject invention can be expressed in suitable host cells using conventional techniques. Any suitable host and/or vector system can be used to express the *Rickettsia felis* outer membrane protein.

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into suitable host cells. For example, DNA encoding the *Rickettsia felis* outer membrane protein can be injected into the nucleus of a host cell or transformed into the host cell using a suitable vector, or mRNA encoding the *Rickettsia felis* outer membrane protein can be injected directly into the host cell, in order to obtain expression of *Rickettsia felis* outer membrane protein in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures. DNA can also be incorporated into artificial lipid vesicles, liposomes, which fuse with the cell membrane, delivering their contents directly into the cytoplasm. In an even more direct approach, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

Further methods for introducing nucleic acid molecules into cells involve the use of viral vectors. One such virus widely used for protein production is an insect virus, baculovirus. For a review of baculovirus vectors, see Miller (1989). Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

Host cells into which the nucleic acid encoding the *Rickettsia felis* outer membrane protein has been introduced can be used to produce the *Rickettsia felis* outer membrane protein.

Having identified the nucleic acid molecules encoding *Rickettsia felis* outer membrane proteins and methods for expressing the *Rickettsia felis* outer membrane proteins encoded thereby, the invention further provides a method of screening a substance (for example, a compound or inhibitor) for the ability of the substance to modify *Rickettsia felis* outer membrane protein function. The method comprises introducing a nucleic acid molecule encoding the *Rickettsia felis* outer membrane protein into a host cell, and expressing the *Rickettsia felis* outer membrane protein encoded by the molecule in the host cell. The cell is then exposed to a substance and evaluated to determine if the substance modifies the function of the *Rickettsia felis* outer membrane protein. From this evaluation, substances effective in altering the function of the *Rickettsia felis* outer membrane protein can be found. Such agents may be agonists or antagonists.

The evaluation of the cell to determine if the substance modifies the function of the *Rickettsia felis* outer membrane protein can be by any means known in the art. The evaluation can comprise the direct monitoring of expression of *Rickettsia felis* outer membrane protein in the host cell, or the evaluation can be indirect.

The nucleic acid molecules of the subject invention can be used either as probes or for the design of primers to obtain DNA encoding other *Rickettsia felis* outer membrane proteins by either cloning and colony/plaque hybridization or amplification using the polymerase chain reaction (PCR).

Specific probes derived from SEQ ID NO:1 can be employed to identify colonies or plaques containing cloned DNA encoding a member of the *Rickettsia felis* outer membrane protein family using known methods (see Sambrook et al. 1989). One skilled in the art will recognize that by employing such probes under high stringency conditions (for example, hybridization at 42° C. with 5×SSPC and 50% formamide, washing at 50–65° C. with 0.5×SSPC), sequences having regions which are greater than 90% homologous or identical to the probe can be obtained. Sequences with lower percent homology or identity to the probe, which also encode *Rickettsia felis* outer membrane proteins, can be obtained by lowering the stringency of hybridization and washing (e.g., by reducing the hybridization and wash temperatures or reducing the amount of formamide employed).

More particularly, in one embodiment, the method comprises selection of a DNA molecule encoding a *Rickettsia felis* outer membrane protein, or a fragment thereof, the DNA molecule having a nucleotide sequence as shown in SEQ ID NO:1, and designing an oligonucleotide probe for *Rickettsia felis* outer membrane protein based on SEQ ID NO:1. A genomic or cDNA library of an organism is then probed with the oligonucleotide probe, and clones are obtained from the library that are recognized by the oligonucleotide probe so as to obtain DNA encoding another *Rickettsia felis* outer membrane protein.

Specific primers derived from SEQ ID NO:1 can be used in PCR to amplify a DNA sequence encoding a member of the *Rickettsia felis* outer membrane protein family using known methods (see Innis et al. 1990). One skilled in the art will recognize that by employing such primers under high stringency conditions (for example, annealing at 50–60° C., depending on the length and specific nucleotide content of the primers employed), sequences having regions greater than 75% homologous or identical to the primers will be amplified.

More particularly, in a further embodiment the method comprises selection of a DNA molecule encoding *Rickettsia felis* outer membrane protein, or a fragment thereof, the DNA molecule having a nucleotide sequence as shown in SEQ ID NO:1, designing degenerate oligonucleotide primers based on regions of SEQ ID NO:1, and employing such primers in the polymerase chain reaction using as a template a DNA sample to be screened for the presence of *Rickettsia felis* outer membrane protein-encoding sequences. The resulting PCR products can be isolated and sequenced to identify DNA fragments that encode polypeptide sequences corresponding to the targeted region of *Rickettsia felis* outer membrane protein.

Various modifications of the nucleic acid and amino acid sequences disclosed herein are covered by the subject invention. These varied sequences still encode a functional *Rickettsia felis* outer membrane protein. The invention thus further provides an isolated nucleic acid molecule encoding a *Rickettsia felis* outer membrane protein, the nucleic acid molecule encoding a first amino acid sequence having at least 90% amino acid identity to a second amino acid sequence, the second amino acid sequence as shown in SEQ ID NO:2. In further embodiments, the first amino acid sequence has at least 95%, 96%, 97%, 98%, or 99% amino acid identity to SEQ ID NO:2.

The invention further provides an isolated DNA oligomer capable of hybridizing to the nucleic acid molecule encoding *Rickettsia felis* outer membrane protein according to the subject invention. Such oligomers can be used as probes in a method of detecting the presence of *Rickettsia felis* outer membrane protein in a sample. More particularly, a sample can be contacted with the DNA oligomer and the DNA oligomer will hybridize to any *Rickettsia felis* outer membrane protein present in the sample, forming a complex therewith. The complex can then be detected, thereby detecting presence of *Rickettsia felis* outer membrane protein in the sample.

The complex can be detected using methods known in the art. Preferably, the DNA oligomer is labeled with a detectable marker so that detection of the marker after the DNA oligomer hybridizes to any *Rickettsia felis* outer membrane protein in the sample (wherein non-hybridized DNA oligomer has been washed away) is detection of the complex. Detection of the complex indicates the presence of *Rickettsia felis* outer membrane protein in the sample. As will be readily apparent to those skilled in the art, such a method could also be used quantitatively to assess the amount of *Rickettsia felis* outer membrane protein in a sample.

For detection, the oligomers can be labeled with, for example, a radioactive isotope, biotin, an element opaque to X-rays, or a paramagnetic ion. Radioactive isotopes are commonly used and are well known to those skilled in the art. Representative examples include indium-111, technetium-99m, and iodine-123. Biotin is a standard label which would allow detection of the biotin labeled oligomer with avidin. Paramagnetic ions are also commonly used and include, for example, chelated metal ions of chromium (III), manganese (II), and iron (III). When using such labels, the labeled DNA oligomer can be imaged using methods known to those skilled in the art. Such imaging methods include, but are not limited to, X-ray, CAT scan, PET scan, NMRI, and fluoroscopy. Other suitable labels include enzymatic labels (horseradish peroxidase, alkaline phosphatase, etc.) and fluorescent labels (such as FITC or rhodamine, etc.).

The invention further provides an isolated *Rickettsia felis* outer membrane protein. The protein is preferably encoded by a nucleotide sequence as shown in SEQ ID NO:1. The protein preferably has an amino acid sequence as shown in SEQ ID NO:2. Further provided is an isolated *Rickettsia felis* outer membrane protein encoded by a first amino acid sequence having at least 90% amino acid identity to a second amino acid sequence, the second amino acid sequence as shown in SEQ ID NO:2. In further embodiments, the first amino acid sequence has at least 95%, 96%, 97%, 98%, or 99% amino acid identity to SEQ ID NO:2.

It should be readily apparent to those skilled in the art that a met residue may need to be added to the amino terminal of the amino acid sequence of the mature *Rickettsia felis* outer membrane protein (i.e., added to SEQ ID NO:2) or an ATG added to the 5' end of the nucleotide sequence (i.e., added to SEQ ID NO:1), in order to express the channel in a host cell. The met version of the mature channel is thus specifically intended to be covered by reference to SEQ ID NO:1 or SEQ ID NO:2.

The invention further provides an antibody or fragment thereof specific for the *Rickettsia felis* outer membrane protein of the subject invention. Antibodies of the subject invention include polyclonal antibodies and monoclonal antibodies capable of binding to the *Rickettsia felis* outer membrane protein, as well as fragments of these antibodies, and humanized forms. Humanized forms of the antibodies of the subject invention may be generated using one of the procedures known in the art such as chimerization. Fragments of the antibodies of the present invention include, but are not limited to, the Fab, the F(ab')$_2$, and the Fc fragments.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell 1984 and St. Groth et al. 1980). Any animal (mouse, rabbit, etc.) which is known to produce antibodies can be immunized with the antigenic *Rickettsia felis* outer membrane protein (or an antigenic fragment thereof). Methods for immunization are well known in the art. Such methods include subcutaneous or intraperitoneal injection of the protein. One skilled in the art will recognize that the amount of the protein used for immunization will vary based on the animal which is immunized, the antigenicity of the protein, and the site of injection.

The protein which is used as an immunogen may be modified or administered in an adjuvant in order to increase the protein's antigenicity. Methods of increasing the antigenicity of a protein are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O—Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al. 1988).

Hybridomas secreting the desired antibodies are cloned and the class and subclass are determined using procedures known in the art (Campbell 1984).

For polyclonal antibodies, antibody containing antisera is isolated from the immunized animal and is screened for the presence of antibodies with the desired specificity using one of the above-described procedures.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, etc. Procedures for accomplishing such labeling are well known in the art, for example see Sternberger et al. 1970, Bayer et al. 1979, Engval et al. 1972, and Goding 1976.

The labeled antibodies or fragments thereof of the present invention can be used for in vitro, in vivo, and in situ assays to identify cells or tissues which express *Rickettsia felis* outer membrane protein, to identify samples containing *Rickettsia felis* outer membrane protein, or to detect the presence of *Rickettsia felis* outer membrane protein in a sample. More particularly, the antibodies or fragments thereof can thus be used to detect the presence of *Rickettsia felis* outer membrane protein in a sample, by contacting the sample with the antibody or fragment thereof. The antibody or fragment thereof binds to any *Rickettsia felis* outer membrane protein present in the sample, forming a complex therewith. The complex can then be detected, thereby detecting the presence of *Rickettsia felis* outer membrane protein in the sample. As will be readily apparent to those skilled in the art, such a method could also be used quantitatively to assess the amount of *Rickettsia felis* outer membrane protein in a sample. As should also be readily apparent, such an antibody may also be used to decrease levels of functional *R. felis* outer membrane protein, by blocking the protein. Such antibodies can therefore be used in the methods of the subject invention to modify levels of functional *R. felis* outer membrane protein.

Further provided is a composition comprising the *Rickettsia felis* outer membrane protein or an antigenic portion thereof and a compatible carrier.

In the methods of the invention, tissues or cells are contacted with or exposed to the composition of the subject invention or a compound. In the context of this invention, to "contact" tissues or cells with or to "expose" tissues or cells to a composition or compound means to add the composition or compound, usually in a liquid carrier, to a cell suspension or tissue sample, either in vitro or ex vivo, or to administer the composition or compound to cells or tissues within an animal (including humans).

For therapeutics, methods of preventing *R. felis* infections by *R. felis* present in a carrier host, the method comprising administering to the carrier host an amount of a compound effective to modify levels of functional *R. felis* outer membrane protein in *R. felis* present in the carrier host, are provided. Further provided are methods of reducing *R. felis* infection of a carrier host, the method comprising administering to the carrier host an amount of a compound effective to prevent function of an *R. felis* outer membrane protein in the carrier host. The formulation of therapeutic compositions and their subsequent administration is believed to be within the skill in the art. In general, for therapeutics, a patient suspected of needing such therapy is given a composition in accordance with the invention, commonly in a pharmaceutically acceptable carrier, in amounts and for periods which will vary depending upon the nature of the particular disease, its severity and the patient's overall condition. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

In addition to such pharmaceutical carriers, cationic lipids may be included in the formulation to facilitate uptake. One such composition shown to facilitate uptake is LIPOFECTIN (BRL, Bethesda Md.).

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual compositions, and can generally be calculated based on $IC_{50}$'s or $EC_{50}$'s in in vitro and in vivo animal studies. For example, given the molecular weight of compound (derived from oligonucleotide sequence and/or chemical structure) and an effective dose such as an $IC_{50}$, for example (derived experimentally), a dose in mg/kg is routinely calculated.

The methods of the subject invention are based on the discovery of an *R. felis* outer membrane protein. Modifying (increasing or decreasing or preventing) "levels" of functional *R. felis* outer membrane protein refers to modifying expression of the protein and/or modifying activity of the protein such as by inhibiting the function of the protein. As used herein, "functional" refers to the synthesis and any necessary post-translational processing of an *R. felis* outer membrane protein in a cell so that the protein functions as it does in its natural state.

Levels of *R. felis* outer membrane protein can be modified by various methods, at the gene and protein levels. In one embodiment, the levels are modified by modifying *R. felis* outer membrane protein gene expression of the *R. felis* outer membrane protein in the cells. This can be accomplished by exposing the cells to a compound which modifies *R. felis* outer membrane protein gene expression of the protein. The compound could be, for example, an antisense oligonucleotide targeted to the *R. felis* outer membrane protein gene. In a similar embodiment, the compound which modifies *R. felis* outer membrane protein gene expression of the *R. felis* outer membrane protein could be a ribozyme.

Other methods for modifying *R. felis* outer membrane protein gene expression could also involve site-directed mutagenesis of the *R. felis* outer membrane protein gene to prevent expression of the *R. felis* outer membrane protein, or various gene therapy techniques.

Levels, in particular activity, of *R. felis* outer membrane protein in the cell can also be modified by exposing the cells to an inhibitor of the *R. felis* outer membrane protein. Inhibitors of the *R. felis* outer membrane protein could readily be identified by screening methods (including the method described above). In addition to chemical inhibitors, peptide inhibitors could also be identified with screening methods (for example, using phage display libraries and other peptide screening methods).

Levels of functional *R. felis* outer membrane protein could also be modified by use of molecules which bind to transcription regulators of the *R. felis* outer membrane protein gene (such as the promoter region of the gene).

In the context of this invention "modulation" or "modifying" generally means inhibition. This modulation can be measured in ways which are routine in the art, for example by Northern blot assay of mRNA expression or Western blot assay of protein expression.

The compounds and/or inhibitors used in the methods of the subject invention encompass any pharmaceutically acceptable salts, esters, or salts of such esters, or any other compound/inhibitor which, upon administration to an animal including a human, is capable of providing (directly or indirectly) the biologically active metabolite or residue thereof. Accordingly, for example, the disclosure is also drawn to prodrugs and pharmaceutically acceptable salts of the compounds and/or inhibitors used in the subject invention, pharmaceutically acceptable salts of such prodrugs, and other bioequivalents.

In regard to prodrugs, the compounds and/or inhibitors for use in the invention may additionally or alternatively be prepared to be delivered in a prodrug form. The term prodrug indicates a therapeutic agent that is prepared in an inactive form that is converted to an active form (i.e., drug) within the body or cells thereof by the action of endogenous enzymes or other chemicals and/or conditions.

In regard to pharmaceutically acceptable salts, the term pharmaceutically acceptable salts refers to physiologically and pharmaceutically acceptable salts of the compounds and/or inhibitors used in the subject invention: i.e., salts that retain the desired biological activity of the parent compound and do not impart undesired toxicological effects thereto.

Drugs, such as peptide drugs, which inhibit the *R. felis* outer membrane protein can be identified by other methods also. For example, a monoclonal antibody can be prepared which specifically hybridizes to the *R. felis* outer membrane protein, thereby interfering with activity. Once a monoclonal antibody which specifically hydridizes to the *R. felis* outer membrane protein is identified, the monoclonal (which is itself a compound or inhibitor which can be used in the subject invention) can be used to identify peptides capable of mimicking the inhibitory activity of the monoclonal antibody. One such method utilizes the development of epitope libraries and biopanning of bacteriophage libraries. Briefly, attempts to define the binding sites for various monoclonal antibodies have led to the development of epitope libraries. Parmley and Smith developed a bacteriophage expression vector that could display foreign epitopes on its surface (Parmley, S. F. & Smith, G. P., Gene 73:305–318 (1988)). This vector could be used to construct large collections of bacteriophage which could include virtually all possible sequences of a short (e.g. six-amino-acid) peptide. They also developed biopanning, which is a method for affinity-purifying phage displaying foreign epitopes using a specific antibody (see Parmley, S. F. & Smith, G. P., Gene 73:305–318 (1988); Cwirla, S. E., et al., Proc Natl Acad Sci USA 87:6378–6382 (1990); Scott, J. K. & Smith, G. P., Science 249:386–390 (1990); Christian, R. B., et al., J Mol Biol 227:711–718 (1992); Smith, G. P. & Scott, J. K., Methods in Enzymology 217:228-257 (1993)).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley, S. F. & Smith, G. P., Gene 73:305–318 (1988); Scott, J. K., Trends in Biochem Sci 17:241–245 (1992)).

Using epitope libraries and biopanning, researchers searching for epitope sequences found instead peptide sequences which mimicked the epitope, i.e., sequences which did not identify a continuous linear native sequence or necessarily occur at all within a natural protein sequence. These mimicking peptides are called mimotopes. In this manner, mimotopes of various binding sites/proteins have been found.

The sequences of these mimotopes, by definition, do not identify a continuous linear native sequence or necessarily occur in any way in a naturally-occurring molecule, i.e. a naturally occurring protein. The sequences of the mimotopes merely form a peptide which functionally mimics a binding site on a naturally-occurring protein.

Many of these mimotopes are short peptides. The availability of short peptides which can be readily synthesized in large amounts and which can mimic naturally-occurring sequences (i.e. binding sites) offers great potential application.

Using this technique, mimotopes to a monoclonal antibody that recognizes *R. felis* outer membrane protein can be identified. The sequences of these mimotopes represent short peptides which can then be used in various ways, for example as peptide drugs that bind to *R. felis* outer membrane protein and decrease the activity of *R. felis* outer membrane protein. Once the sequence of the mimotope is determined, the peptide drugs can be chemically synthesized.

Materials and Methods

Source of Infected Fleas

The infected cat fleas were maintained in the laboratory colony of the Department of Entomology, Louisiana State University Agricultural Center (Henderson & Foil, 1993).

DNA Isolation

A pool of infected cat fleas was washed with sterile phosphate buffered saline (PBS, 137 mm sodium chloride, 2.7 mM potassium chloride, 4.3 mM sodium phosphate dibasic, 1.4 mM potassium phosphate) and homogenized. The homogenate was resuspended in 1 ml of PBS containing 1% sodium dodecyl sulfate (SDS) and 1% proteinase K, placed in a 1.5 ml microcentrifuge tube, and incubated for 1 hr at 37° C. followed by a 10 min incubation at 56° C. A series of phenol/chloroform extractions was performed on the homogenate followed by a single chloroform extraction. The DNA was ethanol precipitated and dried, and the pellet was resuspended in sterile water.

PCR

Amplification of an aliquot of the DNA extracted from fleas using the outer primers for the Rickettsia 17-kDa gene was performed as described previously (Webb et al., 1990; Schriefer et al., 1994b; Higgins et al., 1996). Six micrograms of DNA in a five microliter volume of DNA extract was added to 1×PCR buffer (Boehringer Mannheim, Indianapolis, Ind.), 200 $\mu$M of nucleotide mixture, 10 pmol of each primer, 1.25 units of Taq polymerase (Boehringer Mannheim), and distilled water to a final volume of 100 $\mu$l. The PCR was performed in a DNA Thermal Cycler (Perkin-Elmer Cetus, Norwalk, Conn.). The PCR product from this reaction was further amplified using a set of nested primers for the 17 kDa gene (Higgins et al., 1996). The PCR conditions for both reactions were as previously described (Webb et al., 1990; Schriefer et al., 1994b; Higgins et al., 1996).

Genome Walking

One region of the *R. felis* rompA gene, the promoter and ATG start site, was amplified by the utilization of a Genome Walker kit (Clonetech, Palo Alto, Calif.). The primers are listed in Table 1. The DNA extract from the fleas was divided into five aliquots and subjected to digestion by five blunt end cutting restriction enzymes (Dra I, EcoR V, Pvu II, Sca I, Str I) at 37° C. overnight. The reaction mixtures were subjected to a series of phenol/chloroform extractions followed by a chloroform extraction and ethanol precipitation. Adapters from the kit were ligated to the digested DNA samples at 16° C. overnight. The reaction was stopped by incubating the samples at 70° C. for 5 min, followed by the addition of Tris-EDTA buffer (10 mM Tris/HCl, 1 mM EDTA, pH 8.0). Each sample was PCR-amplified in the primary reaction using the Advantage™ Tth polymerase kit (Clonetech, Palo Alto, Calif.) with the primary R. felis rompA gene specific primer (GSP1) and adapter primer 1 (AP1) from the kit. The nested PCR was performed as above with the addition of one µl of the primary reactions as the template and the substitution of nested primers GSP2 and AP2 for the GSP1 and AP1 primers. The cycling parameters utilized were modified from those proposed in the manufacturer's instructions with the annealing temperature being increased to 3° C. higher than the instructions. The sequences of the primers are listed in Table 1.

Sequencing of the rompA Gene

The DNA extracts from the infected cat fleas were utilized for sequencing the R. felis rompA gene. Primers designed for amplification of the repeat region and 5' region of the gene were from published sequences or were generated from sequence analysis of the R. felis PCR products (Table 1). The PCR amplification conditions for the reactions were 1 cycle at 95° C. for 5 min, 30 cycles of 1 min at 95° C., 20 sec at 48° C., 3 min at 72° C. followed by 1 cycle of 5 min at 72° C. and 1 soak cycle at 4° C. An aliquot of the PCR products were analyzed by resolution on 1.3% (w/v) agarose gels that were stained with ethidium bromide and visualized by an ultraviolet light source. The remaining PCR products were cloned using the TOPO™ TA Cloning Kit (Invitrogen, Carlsbad, Calif.) and plated on selective media containing ampicillin and X-Gal/IPTG overnight at 37° C. Positive clones were selected and grown in LB medium containing ampicillin. Plasmid DNA was isolated using the High Pure™ Plasmid Isolation kit (Roche Molecular Biochemicals, Indianapolis, Ind.) and digested with EcoRI according to the manufacturer's instructions. The restriction enzyme digests were analyzed in a 1.3% (w/v) agarose gel. Plasmids that contained DNA inserts were sequenced twice using an ABI automated sequencer (ABI, Foster City, Calif.) using M13 and T7 sequencing primers (Gibco/BRL, Grand Island, N.Y.).

Genetic Analysis

The primer design sequence alignment and preliminary comparison was facilitated through the use of the software programs GCG (Wisconsin Package, Version 10.0, Genetics Computer Group, Madison, Wis.) and Lasergene (DNAstar, Madison, Wis.), which are built upon the CLUSTAL algorithm platform (Higgins & Sharp, 1989). The percentages of similarity were determined by CLUSTAL method.

Phylogenetic Analysis

Phylogenetic analyses were performed using the maximum parsimony and distance program of the PAUP 4.1 software (Swofford et al., 1998). Distance matrix analyses were generated with the Kimura 2 parameter model for multiple substitutions (Kimura, 1980). Bootstrap values (Felsenstein et al., 1985) based on the analysis of 1,000 replicates were determined to estimate the node reliability of the phylogenetic trees obtained by the parsimony, maximum-likelihood, and distance methods.

GenBank Accession Numbers

The Genbank accession numbers of the 17-kDa protein gene sequences are: R. australis, M74042, M28480 (Anderson & Tzianabos, 1989); R. massiliae Mtu1, U11017; R. parkeri, U17008; R. rickettsii, M16486 (Anderson et al., 1987); R. typhi, M28481 (Anderson & Tzianabos, 1989); and R. felis 17-kDa protein gene (AF195118, this study).

The Genbank accession numbers of all rickettsial rompA sequences compared are: R. aeschlimanii MC16, U83446, U43800 (Fournier et al., 1998); R. africae ESF, U83436, U43790 (Fournier et al., 1998); R. akari Kaplan, L01461 (Gilmore, 1993) R. australis PHS, AF149108 (Stenos & Walker, 2000); R. conorii Astrakhan, U83437, U43791 (Fournier et al., 1998); R. conorii Israeli, U43797, U83441 (Fournier et al., 1998); R. conorii Malish 7, U01028 (Crocquet-Valdes et al., 1994); R. conorii Moroccan, U83443, U43798 (Fournier et al., 1998); R. honei RB, AF018075, AF018076 (Stenos et al., 1998); R. japonica U43795, U83442 (Fournier et al., 1998); R. massiliae Bar29, U43792, U83444 (Fournier et al., 1998); R. massiliae Mtu1, U83445, U43799 (Fournier et al., 1998); R. montanesis, U43801, U83447 (Fournier et al., 1998); R. parkeri, U43802, U83449 (Fournier et al., 1998); R. prowazekii, M28482 (Anderson & Tzianabos, 1989); R. rhipicephali, U43803, U83450 (Fournier et al., 1998); R. rickettsii M31227 (Anderson et al., 1990); R. sibirica 246, U43807, U83455 (Fournier et al., 1998); R. sibirica mongolotimonae, U43796, U83439 (Fournier et al., 1998); R. slovaca 13-B, U43808, U83454 (Fournier et al., 1998); and R. felis rompA (AF191026, this study).

Transmission Electron Microscopy

Adult fleas and larvae were anesthesized on dry ice, their heads were removed, and they were immediately dissected in a drop of fixative. Midguts with adjacent tissues were fixed in a mixture of 1.25% (v/v) formaldehyde, 2.5% (v/v) glutaraldehyde, 0.03% trinitrophenol and 0.03% $CaCl_2$ in 0.05 M cacodylate buffer, pH 7.3 (Ito & Rikihisa, 1981), postfixed in 1% $OSO_4$ in the same buffer, stained en bloc with 1% uranyl acetate in 0.1 M maleate buffer (0.1 M maleic acid), pH 5.2, dehydrated in ethanol and embedded in Spurr low viscosity epoxy resin (Polysciences, Warrington, Pa.). Ultrathin sections were cut on Reichert Ultracut S ultramicrotome, stained with uranyl acetate and lead citrate, and examined in a Philips 201 electron microscope at 60 kV.

EXAMPLE I

Genetic Analysis

In order to verify that the DNA isolated from the fleas contained R. felis genomic DNA, RFLP analysis was performed on the 17-kDa protein gene PCR product. The flea DNA extract amplified using rickettsial specific primers yielded a 434 base pair (bp) product. This product was then amplified by nested primers resulting in a 231 bp product. The nested product was then digested using the restriction enzymes, AluI and XbaI, and was resolved by agarose gel electrophoresis. This method yielded a pattern that was characteristic of R. felis and was distinctive from that of the R. typhi 17-kDa protein gene PCR product (Schriefer et al., 1994b; Higgins et al., 1996). Once the DNA was confirmed to be that of R. felis, phylogenetic analysis using parsimony was conducted on the sequence. Due to the limited number of 17 kDa protein genes in Genbank, only nine Rickettsia species were analyzed. The Kimura 2 model analysis placed R. felis in the SFG of rickettsiae with only 5.3% divergence from R. australis. The R. felis 17-kDa protein gene was only 5.3 to 6.6% divergent from the other SFG rickettsiae, but was 11.3 and 11.5% divergent from R. typhi and R. prowazekii, respectively.

Initially sequence was generated for the R. felis rompA gene through the utilization of primers designed for the sequencing of the R. australis rompA gene (Bouyer et al., 1999; Stenos & Walker, 2000). This generated a 1279 bp fragment. The amplification strategy for the rest of the R. felis rompA gene involved the use of published primers that were shown to have been effective for delineating other rickettsial rompA genes (Regnery et al., 1991; Walker et al., 1995). A set of primers was also developed by this laboratory from the published R. rickettsii rompA sequence (Anderson et al., 1990) and from the generated R. felis sequence. A region of the R. felis rompA gene sequence that was difficult to amplify was obtained by genome walking. This sequencing strategy yielded a DNA sequence of 5513 bp (SEQ ID NO:3) with a G+C content of 39.49%. The gene had an open reading frame (ORF) of 1860 bp (SEQ ID NO:1; encoding amino acid SEQ ID NO:2)(G+C content of 40.27%) that was found to contain four repeat units, which consisted of two complete repeat units (225 and 216 bp) and two repeat units containing deletions of 6 and 69 bp, resulting in altered units of 219 and 147 bp in size. The promoter region of the R. felis rompA gene was found to be similar to that of the R. australis rompA gene (Stenos & Walker, 2000). The coding sequences for the putative ribosomal binding site, −10 sequence and −35 region shared 100% homology between those two species. Genetic analysis of the full length R. felis rompA gene open reading frame (ORF, 1860 bp) and its comparison with other SFG rompA gene ORFs that have been sequenced was problematic due to the fact that the R. felis gene contained a premature stop codon, thereby resulting in a much smaller coding region than R australis (6320 bp), R. conorii Malish 7 strain (6065 bp) and R. rickettsii (6749 bp). The R. felis rompA gene ORF was found to have 51.6%, 48.6%, 37.9% similarity to R. rickettsii, R. conorii, and R. australis, respectively. The marked divergence from R. australis is explained by its having the most divergent of rickettsial rompA repeat domains (Stenos & Walker, 2000). It was determined that the most effective means to analyze the R. felis rompA gene would be to convert the gene into protein domains and combine the areas of interest outside of the repeats. The rickettsial rOmpA proteins were divided using the pattern suggested by Anderson (Anderson et al., 1990). The domains were linked using the method of Fournier (1998). Domain I of each rOmpA protein started at the initial methionine (residue 1) of the ORF and ended at the beginning of the repeat region. The domain I-domain III rompA fusions comprised 340 amino acids residues in length, which corresponds with the size of the protein that would be encoded by R. felis minus the repeat domain. This approach allowed the protein segments analyzed to be closer in size: R. felis domain I, being 206 amino acid residues; R. rickettsli and R. conorii, 211 residues; and R. australis, 265 residues in length. The entire repeat region of each of the rOmpA proteins was considered as domain II. The hydrophobic region that immediately follows the repeat domain is domain III. This region contained the premature stop codon in the R. felis rompA. Domain IV of the R. felis rOmpA, which was not used in the analysis because it contained several stop codons, consisted of primarily hydrophilic regions. Amino acid sequences of the R. fells rOmpA were analyzed for percent similarity utilizing the CLUSTAL algorithm (Higgins & Sharp, 1989). Comparison of the R. felis rOmpA domain I with that of other Rickettsia species showed a 36.4% similarity with R. australis, 40.8% similarity to R. conorii (Malish 7 strain) and a 41.7% similarity with R. rickettsii on the amino acid level. Phylogenetic trees constructed from parsimony and distance analysis both indicate that R. felis is nearer to R. australis. This is confirmed by the Kimura-2 parameter model (Kimura, 1980).

The repeat region (domain II) of the R. felis rOmpA is unique by several criteria when compared to other rOmpA repeat domains. The repeat region is smaller than in other published naturally occurring species as it contains only three complete or near complete repeat units and one partial repeat unit. The first repeat is a type I. The second repeat unit is homologous to a type I repeat with the deletion of two amino acids being the only difference. The third repeat is of type IIa and is 72 amino acids long. Comparison of the partial fourth repeat to a type IIb unit showed that it had a deletion of 23 amino acids. The domain III of the R. felis rompA protein is most similar to R. australis (46.2%).

EXAMPLE II

Electron Microscopy

In adult cat fleas, rickettsiae were found in midgut epithelial cells in underlying tissues, including muscles, and in oocytes. In larvae, rickettsiae mostly were localized in midgut epithelial cells. Rickettsiae were typically located free in the cytosol surrounded by electron-lucent clear spaces. They varied in length and width and density of the cytoplasm, some rickettsiae in larvae having dense cytoplasm. Also rickettsiae in larvae were observed to have intracytoplasmic vacuoles.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

Primers for amplification of R. felis rompA gene

Promoter region and ATG start site

Primer GSP1 (RF321-292)
SEQ ID NO:4: AGCTCCTCCCGTATCTACCACTGAACCTAA

Primer ASP1 (Invitrogen)
SEQ ID NO: 5: GTAATACGACTCACTATAGGGC

Primer GSP1 (RFG5-38r)
SEQ ID NO:6: AGCTCCTCCCGTATCTACCACTGAACCTAA

Primer ASP2 (Invitrogen)
SEQ ID NO: 7: ACTATAGGGCACGCGTGGT

5' region

Primer 190.70 (Regnery et al. 1991)
SEQ ID NO:8: ATGGCGAATAATTCTCCAAAA

Primer 190.602n (Regnery et al. 1991)
SEQ ID NO:9: AGTGCAGCAATTCGCTCCCCT

5'-Repeat region overlap

Primer Rf247f
SEQ ID NO:10: AATAATTTTGCAGCAGGTCTTT

Primer RE Repeat r
SEQ ID NO:11: TGACTCAATGCTCCACTTTAGAT

Repeat region

Primer 675 (Walker et al. 1995)
SEQ ID NO:12: CCAGACAGATGCTGCCATTAAGC

TABLE 1-continued

Primers for amplification of R. felis rompA gene

Primer 2940 (Walker et al. 1995)
SEQ ID NO:13: TTCCGATCTAGACTTCCTCCAAGC
Repeat-3' overlap Primer RF-Repeat f
SEQ ID NO: 14: AGGCGGTGATAATGTAGGTGTCT Primer RfB5-27R
SEQ ID NO:15: TTACTCGCAGCTCCAAAATCTAT
3' Region (1.4 kb)

Primer RR-3622 f
SEQ ID NO:16: GCTGGAGGAAGCCTAGCTGCC

Primer RR-4999r
SEQ ID NO:17: TGACCAACCGAATTAGCCGC
3' region (1.2 kb)

Primer F3-4936 (Stenos and Walker 2000)
SEQ ID NO:18: GGTGGTCAGGCTCTGAAGCTAAAAC

Primer B21-6324 (Stenos and Walker 2000)
SEQ ID NO:19: TGCAGTTTGATAACCGACAGTCTC
3' region (1.0 kb)

Primer 6049
SEQ ID NO:20: ACTGGTGGCACTATAGGTTTTGAC

Primer 7019
SEQ ID NO:21: ATCGGCAGTTTTTCTAATAATAAT

REFERENCES

Adams et al., Am J Trop Med Hyg 43:400–409 (1990).

Anderson et al., J Bacteriol 169:2385–2390 (1987).

Anderson and Tzianabos, J Bacteriol 171:5199–5201 (1989).

Anderson et al., Infect Immun 58:2760–2769 (1990).

Andersson and Andersson, Mol Biol Evol 16:1178–1191 (1999).

Andersson et al., Mol Biol Evol 16:987–995 (1999).

Azad et al., Proc Natl Acad Sci USA 89:43–46 (1992).

Bayer, E. A., et al., Meth Enzym 62:308 (1979).

Bouyer et al., In *Rickettsiae and Rickettsial Disease at the turn of the Third Millennium*, pp. 11–15, Eds. Raoult and Brouqui, Elsevier, Paris, France (1999).

Campbell, A. M., *Monoclonal Antibody Technology: Laboratory Techniques in Biochemistry and Molecular Biology*, Elsevier Science Publishers, Amsterdam, The Netherlands (1984).

Capecchi, M., Cell 22:479–488 (1980).

Chrisey, L., et al., Antisense Research and Development 1(1): 57–63 (1991).

Christoffersen, R. E. and Marr, J. J., Journal of Medicinal Chemistry 38(12): 2023–2037 (1995).

Crocquet-Valdes et al., Gene 140:115–119 (1994).

Engval, E., et al., Immunol 109:129 (1972).

Felsenstein, Evolution 39:783–791 (1985).

Fournier et al., Int J Syst Bacteriol 48:839–849 (1998).

Gilmore, Gene 125:97–102 (1993).

Goding, J. W., J Immunol Meth 13:215 (1976).

Han, L., et al., Proc Natl Acad Sci USA 88:4313–4317 (1991).

Henderson and Foil, J Med Entomol 30:619–621 (1993).

Higgins and Sharp, CALBIOS 5:151–153 (1989).

Higgins et al., J Clin Microbiol 34:671–674 (1996).

Innis, et al., *PCR Protocols*, Academic Press, San Diego, Calif. (1990).

Ito and Rikihisa, In *Rickettsiae and rickettsial diseases*, pp. 213–227, Eds. Burgdorfer and Anacker, Academic Press, Inc., New York, N.Y. (1981).

Kimura, J Mol Evol 16:111–120 (1980).

Klein, T. M., et al., Nature 327:70–73 (1987).

Lutz, et al., Exp Cell Res 175:109–124 (1988).

Mannino, R. J. and Gould-Fogerite, S., BioTechniques 6:682–690 (1988).

Miller, L. K., Bioessays 11:91–95 (1989).

Needleman and Wunach, J Mol Biol 48:443 (1970).

Noden et al., J Med Entomol 35:410–414 (1998).

Pearson and Lipman, Proc Natl Acad Sci USA 85:2444 (1988).

Radulovic et al., Antimicrob Agents Chemother 39:2564-2566 (1995a).

Radulovic et al., Infect Immun 63:4826–4829 (1995b).

Regnery et al., J Bacteriol 173:1576–1589 (1991).

Rossi, J. J., et al., AIDS Research and Human Retroviruses 8(2): 183–189 (1992).

Rossi, J. J., British Medical Bulletin 51(1): 217–225 (1995).

Sambrook et al., *Molecular Cloning: A Laboratory Manual*, 2d Edition, Cold Spring Harbor Laboratory Press, Cold Spring Harbor, N.Y. (1989).

Sarver, N., et al., Science 247:1222–1225 (1990).

Schriefer et al., J Clin Microbiol 32:949–954 (1994b).

Schriefer et al., J Med Entomol 31:681–685 (1994a).

Shigekawa, K. and Dower, W. J., BioTechniques 6:742–751 (1988).

Smith and Waterman, Adv Appl Math 2:482 (1981).

Stenos et al., Int J Syst Bacteriol 48:1399–1404 (1998).

Stenos and Walker, Int J Syst Evol Microbiol 50:1776–1779 (2000).

Sternberger, L. A., et al., J Histochem Cytochem 18:315 (1970).

St. Groth, et al., J Immunol Methods 35:1–21 (1980).

Swofford, *PAUP: Phylogenetic analysis using parsimony (and other methods)*, Version 4, Sinauer Associates, Sunderland, Mass. (1998).

Walker et al., Am J Trop Med Hyg 52:569–576 (1995).

Webb et al., J Clin Microbiol 28:530–534 (1990).

Williams et al., J Clin Microbiol 30:1758–1762 (1992).

What is claimed is:

1. An isolated nucleic acid molecule encoding a *Rickettsia felis* outer membrane protein having a amino acid sequence as shown SEQ ID NO:2 or having 90% amino acid identity with SEQ ID NO:2.

2. The isolated nucleic acid molecule of claim 1 wherein said nucleic acid is deoxyribonucleic acid.

3. The isolated nucleic acid molecule of claim 2 wherein said deoxyribonucleic acid is cDNA.

4. The isolated nucleic acid molecule of claim 3 wherein said nucleic acid molecule comprises SEQ ID NO:1.

5. The isolated nucleic acid molecule of claim 1 wherein said nucleic acid is ribonucleic acid.

6. The isolated nucleic acid molecule of claim 5, wherein said ribonucleic acid is mRNA.

7. An isolated nucleic acid module fully complementary to the mRNA of claim 6.

8. A host cell comprising the nucleic acid molecule of claim 7.

9. An expression vector comprising the nucleic acid molecule of claim 7.

10. A host cell comprising the expression vector of claim 9.

11. A host cell comprising the nucleic acid molecule of claim 1.

12. An expression vector comprising the nucleic acid molecule of claim 1.

13. A host cell comprising the expression vector of claim 12.

14. A method of increasing expression of *Rickettsia felis* outer membrane protein in a host cell, said method comprising:
    introducing the nucleic acid molecule of claim 1 into the cell; and
    allowing said cell to express said nucleic acid molecule resulting in the production of *Rickettsia felis* outer membrane protein in said cell.

15. A method of screening a substance for the ability of the substance to modify *Rickettsia felis* outer membrane protein function, said method comprising:
    introducing the nucleic acid molecule of claim 1 into a host cell;
    expressing said *Rickettsia felis* outer membrane protein encoded by said nucleic acid molecule in the host cell;
    exposing the cell to a substance; and
    evaluating the exposed cell to determine if the substance modifies the function of the *Rickettsia felis* outer membrane protein.

16. The method of claim 15 wherein said evaluation comprises monitoring the expression of *Rickettsia felis* outer membrane protein.

* * * * *

SEQUENCE LISTING

<160> NUMBER OF SEQ ID NOS: 21

<210> SEQ ID NO 1
<211> LENGTH: 1920
<212> TYPE: DNA
<213> ORGANISM: Rickettsia felis

<400> SEQUENCE: 1

| | | | | | |
|---|---|---|---|---|---|
| atggcgaata | tttctctaaa | attatttcaa | aaagcaattc | aaaaaggtct | taaaactgct | 60 |
| ttattcacca | cctcaaccgc | agcgataatg | ctaaccggta | gtggagtcct | tggtgctgca | 120 |
| agaaccgtaa | ctgctgatgg | tgcagagctt | gcagccggaa | caaatatagg | tcctggagcc | 180 |
| ggtgcttttg | tagcgggttc | tactttacaa | tataccggtg | cttttacggt | tactgatgct | 240 |
| gacgtaagtg | ttcgtgcatt | agatttaaat | aattttgcag | caggtctttt | ttcagtaact | 300 |
| ggtgatattt | cattaggttc | agtggtagat | acgggaggag | ctaataaact | tgcagttaat | 360 |
| attgatgatg | gtttaacctt | aactttaaca | ggtaccggta | ctgcagccta | cggtgcaaat | 420 |
| cctgcgttgt | tattccaagg | tggacaagct | gctgctaata | atacatatac | tgctttaggt | 480 |
| aatataactc | taggtggagc | gaatgccggt | ttgactattg | cttcagatcc | agatgtatta | 540 |
| ggaccaataa | cgcttgcagg | aaatatagat | ggaggaggta | taataactga | caatacagat | 600 |
| gctgccatta | acggaacaat | aggtaatact | aatccggcag | ctcaaataag | cattggagca | 660 |
| agtacgcttt | ctcttggagg | ggcagttatt | aaagccacta | cgactaagtt | aacaaatgca | 720 |
| gcgccggtat | taacacttac | aaatgcaaat | gcagtattaa | caggtgctgt | tgataacacc | 780 |
| acaggcggtg | atgatgtagg | tgtcttaaat | ttaaacggag | cgttgagtca | agtaactgga | 840 |
| aatataggta | atacaaattc | attagcgaca | ataagtgtag | gagcaggtac | ggctacgtta | 900 |
| gggggagcgg | ttattaaagc | cactacgact | aagttaacga | atgcagcgtc | ggtattaaca | 960 |
| cttacaaatg | cagtattaac | aggtgctgtt | gataacacca | caggcggtga | taatgtaggt | 1020 |
| gtcgtaaatc | taagtggagc | attgagtcaa | gtaccggga | atataggtaa | tacaaattca | 1080 |
| ttagccacga | taaatatagg | agcaggtgtg | gctaccttgg | atggagcggt | tattaaagct | 1140 |
| actacgacta | agttaacaga | tgatgcgtca | gtattaatat | ttacgaatcc | tgtagtagta | 1200 |
| accggagcaa | tagataatac | cggtaatgcc | aataaaggtg | tggtaatctt | taccggagca | 1260 |
| agtacggtaa | ccgataatat | aggtaacacg | gcagtattag | cagaggtaag | cgtaggagca | 1320 |
| ggtttgctgc | aaatacaagg | cggagtagta | aaagcgaatg | caataaactt | aacggataat | 1380 |
| gcgtcagtag | taacatttac | cggtgatagt | acgtaacag | gtagtatagg | tggtacagaa | 1440 |
| ctcttcgcaa | cagtgaatat | aggagcagga | ataacattac | gagccggagg | aagcctagct | 1500 |
| gcgaataata | tagattttgg | agctgcgagt | aatttagagt | ttaacggtcc | tgccggtaag | 1560 |
| aattataact | taatcggaac | tatagcaaac | ggtaataatg | ctacacttaa | tattaatgct | 1620 |
| gctggtacag | tgattgcaaa | tgatgttagt | ataggcacag | ttgcacaaat | taacattcaa | 1680 |
| aataataaga | tttttgtaat | aaatgctaag | aacgctgatg | ttgatatatt | agacgctcag | 1740 |
| gcgattagtt | ttaaaggagc | agcttcacgt | cttttcttag | ctaacgttag | tctacagatg | 1800 |
| atagagttat | cactcttaaa | aatcatttac | ccggtcttgc | taacgtggt | ggtgagttaa | 1860 |
| ttcttttgag | tccaacaaaa | cttatgaccg | tacaaggtga | cgttggagct | aaaacaatag | 1920 |

<210> SEQ ID NO 2
<211> LENGTH: 619

-continued

```
<212> TYPE: PRT
<213> ORGANISM: Rickettsia felis

<400> SEQUENCE: 2

Met Ala Asn Ile Ser Leu Lys Leu Phe Gln Lys Ala Ile Gln Lys Gly
  1               5                  10                  15

Leu Lys Thr Ala Leu Phe Thr Thr Ser Thr Ala Ala Ile Met Leu Thr
             20                  25                  30

Gly Ser Gly Val Leu Gly Ala Ala Arg Thr Val Thr Ala Asp Gly Ala
         35                  40                  45

Glu Leu Ala Ala Gly Thr Asn Ile Gly Pro Gly Ala Gly Ala Phe Val
     50                  55                  60

Ala Gly Ser Thr Leu Gln Tyr Thr Gly Ala Phe Thr Val Thr Asp Ala
 65                  70                  75                  80

Asp Val Ser Val Arg Ala Leu Asp Leu Asn Asn Phe Ala Ala Gly Leu
                 85                  90                  95

Phe Ser Val Thr Gly Asp Ile Ser Leu Gly Ser Val Val Asp Thr Gly
            100                 105                 110

Gly Ala Asn Lys Leu Ala Val Asn Ile Asp Asp Gly Leu Thr Leu Thr
        115                 120                 125

Leu Thr Gly Thr Gly Thr Ala Ala Tyr Gly Ala Asn Pro Ala Leu Leu
    130                 135                 140

Phe Gln Gly Gly Gln Ala Ala Ala Asn Asn Thr Tyr Thr Ala Leu Gly
145                 150                 155                 160

Asn Ile Thr Leu Gly Gly Ala Asn Ala Gly Leu Thr Ile Ala Ser Asp
                165                 170                 175

Pro Asp Val Leu Gly Pro Ile Thr Leu Ala Gly Asn Ile Asp Gly Gly
            180                 185                 190

Gly Ile Ile Thr Asp Asn Thr Asp Ala Ala Ile Asn Gly Thr Ile Gly
        195                 200                 205

Asn Thr Asn Pro Ala Ala Gln Ile Ser Ile Gly Ala Ser Thr Leu Ser
    210                 215                 220

Leu Gly Gly Ala Val Ile Lys Ala Thr Thr Thr Lys Leu Thr Asn Ala
225                 230                 235                 240

Ala Pro Val Leu Thr Leu Thr Asn Ala Asn Ala Val Leu Thr Gly Ala
                245                 250                 255

Val Asp Asn Thr Thr Gly Gly Asp Asp Val Gly Val Leu Asn Leu Asn
            260                 265                 270

Gly Ala Leu Ser Gln Val Thr Gly Asn Ile Gly Asn Thr Asn Ser Leu
        275                 280                 285

Ala Thr Ile Ser Val Gly Ala Gly Thr Ala Thr Leu Gly Gly Ala Val
    290                 295                 300

Ile Lys Ala Thr Thr Thr Lys Leu Thr Asn Ala Ala Ser Val Leu Thr
305                 310                 315                 320

Leu Thr Asn Ala Val Leu Thr Gly Ala Val Asp Asn Thr Thr Gly Gly
                325                 330                 335

Asp Asn Val Gly Val Val Asn Leu Ser Gly Ala Leu Ser Gln Val Thr
            340                 345                 350

Gly Asn Ile Gly Asn Thr Asn Ser Leu Ala Thr Ile Asn Ile Gly Ala
        355                 360                 365

Gly Val Ala Thr Leu Asp Gly Ala Val Ile Lys Ala Thr Thr Thr Lys
    370                 375                 380

Leu Thr Asp Asp Ala Ser Val Leu Ile Phe Thr Asn Pro Val Val Val
385                 390                 395                 400
```

```
Thr Gly Ala Ile Asp Asn Thr Gly Asn Ala Asn Lys Gly Val Val Ile
            405                 410                 415
Phe Thr Gly Ala Ser Thr Val Thr Asp Asn Ile Gly Asn Thr Ala Val
            420                 425                 430
Leu Ala Glu Val Ser Val Gly Ala Gly Leu Leu Gln Ile Gln Gly Gly
            435                 440                 445
Val Val Lys Ala Asn Ala Ile Asn Leu Thr Asp Asn Ala Ser Val Val
450                 455                 460
Thr Phe Thr Gly Asp Ser Thr Val Thr Gly Ser Ile Gly Gly Thr Glu
465                 470                 475                 480
Leu Phe Ala Thr Val Asn Ile Gly Ala Gly Ile Thr Leu Arg Ala Gly
            485                 490                 495
Gly Ser Leu Ala Ala Asn Asn Ile Asp Phe Gly Ala Ala Ser Asn Leu
            500                 505                 510
Glu Phe Asn Gly Pro Ala Gly Lys Asn Tyr Asn Leu Ile Gly Thr Ile
            515                 520                 525
Ala Asn Gly Asn Asn Ala Thr Leu Asn Ile Asn Ala Ala Gly Thr Val
            530                 535                 540
Ile Ala Asn Asp Val Ser Ile Gly Thr Val Ala Gln Ile Asn Ile Gln
545                 550                 555                 560
Asn Asn Lys Ile Phe Val Ile Asn Ala Lys Asn Ala Asp Val Asp Ile
            565                 570                 575
Leu Asp Ala Gln Ala Ile Ser Phe Lys Gly Ala Ala Ser Arg Leu Phe
            580                 585                 590
Leu Ala Asn Val Ser Leu Gln Met Ile Glu Leu Ser Leu Leu Lys Ile
            595                 600                 605
Ile Tyr Pro Val Leu Leu Thr Val Val Ser
        610                 615

<210> SEQ ID NO 3
<211> LENGTH: 5513
<212> TYPE: DNA
<213> ORGANISM: Rickettsia felis

<400> SEQUENCE: 3
ggctggtaaa aaatctcgat gtcatccccg cgtggatacc gatgtcattc ctgcgaaagc      60
aggaatccag cataaagcga gataaattga gcttttaatt tcaaaaattt tatgtattta     120
tacttttttt ctggattcct gctttcgcag gaatgacata agagcattt accggtctac      180 acaacaatgc cttgcgagga gcgaagcgac gtggcaatct agaaaaaata ataaaaaaat     240
tctgtaaatc agaattttta actggattgc ttcgtcgaat tactatgtaa ttcttctcgc     300
aatgacgaaa aaacgagcca tacaacaaag ctaccgcccc tgcagaatgc aaatgccaca     360
tattcatact aaatttgtaa agtattatat ataattatta attataatag acatattaaa     420
aaaattgtat taaaattgta acaattacta agttattta ttttattaa ggtatatatg     480 gcgaatattt ctctaaaatt atttcaaaaa gcaattcaaa aagggtcttaa aactgcttta     540 ttcaccacct caaccgcagc gataatgcta accggtagtg gagtccttgg tgctgcaaga     600
accgtaactg ctgatggtgc agagcttgca gccggaacaa atataggtcc tggagccggt     660
gcttttgtag cgggttctac tttacaatat accggtgctt ttacggttac tgatgctgac     720
gtaagtgttc gtgcattaga tttaaataat tttgcagcag gtcttttttc agtaactggt     780
gatatttcat taggttcagt ggtagatacg ggaggagcta ataaacttgc agttaatatt     840
```

-continued

```
gatgatggtt taaccttaac tttaacaggt accggtactg cagcctacgg tgcaaatcct    900
gcgttgttat tccaaggtgg acaagctgct gctaataata catatactgc tttaggtaat    960
ataactctag gtggagcgaa tgccggtttg actattgctt cagatccaga tgtattagga   1020
ccaataacgc ttgcaggaaa tatagatgga ggaggtataa taactgacaa tacagatgct   1080
gccattaacg gaacaatagg taatactaat ccggcagctc aaataagcat tggagcaagt   1140
acgctttctc ttggaggggc agttattaaa gccactacga ctaagttaac aaatgcagcg   1200
ccggtattaa cacttacaaa tgcaaatgca gtattaacag gtgctgttga taacaccaca   1260
ggcggtgatg atgtaggtgt cttaaattta aacggagcgt tgagtcaagt aactggaaat   1320
ataggtaata caaattcatt agcgacaata agtgtaggag caggtacggc tacgttaggg   1380
ggagcggtta ttaaagccac tacgactaag ttaacgaatg cagcgtcggt attaacactt   1440
acaaatgcag tattaacagg tgctgttgat aacaccacag gcggtgataa tgtaggtgtc   1500
gtaaatctaa gtgagcatt gagtcaagta accgggaata taggtaatac aaattcatta   1560
gccacgataa atataggagc aggtgtggct accttggatg gagcggttat taaagctact   1620
acgactaagt taacagatga tgcgtcagta ttaatattta cgaatcctgt agtagtaacc   1680
ggagcaatag ataataccgg taatgccaat aaaggtgtgg taatctttac cggagcaagt   1740
acggtaaccg ataatatagg taacacggca gtattagcag aggtaagcgt aggagcaggt   1800
ttgctgcaaa tacaaggcgg agtagtaaaa gcgaatgcaa taaacttaac ggataatgcg   1860
tcagtagtaa catttaccgg tgatagtacg gtaacaggta gtataggtgg tacagaactc   1920
ttcgcaacag tgaatatagg agcaggaata acattacgag ccggaggaag cctagctgcg   1980
aataatatag atttttggagc tgcgagtaat ttagagtttta acggtcctgc cggtaagaat   2040
tataacttaa tcggaactat agcaaacggt aataatgcta cacttaatat taatgctgct   2100
ggtacagtga ttgcaaatga tgttagtata ggcacagttg cacaaattaa cattcaaaat   2160
aataagattt ttgtaataaa tgctaagaac gctgatgttg atatattaga cgctcaggcg   2220
attagtttta aaggagcagc ttcacgtctt tcttagctaa acgttagtct acagatgata   2280
gagttatcac tcttaaaaat catttacccg gtcttgctaa cggtggtggt gagttaattc   2340
ttttgagtcc aacaaaactt atgaccgtac aaggtgacgt tggagctaaa acaataggta   2400
cggcaggaaa tgaattagca tcattaagtg ttttaggtaa tgtagcattg aataatatag   2460
atgctacaaa tgttcctgta tttaatatcc taaatgttac aaactttgtt gatgtaggtg   2520
ggattactaa tcaaattaat gtaataaata acggtgctgc aggccgtatg gcctacaggt   2580
ggagcgattc ctggccgctg cggttcttat acgattgatg caaatggcgg taatgtagga   2640
attttagcca acggtcagaa tattaatttt ggctcttgaa gatgccactt tagtattaca   2700
aaatagtgca gcccggtacc ggtacgatac cattaaatgc tgtacttgat ccactagctc   2760
caagtaaagg taagcttgct gtagattcag aagctgcggg cgggaaagta attcttgcaa   2820
gtgtcgaaat gctacttacg ggtactgcag taaataaatt aaaagaatta gaatttagag   2880
gaaacggaac attccaaata gatactgaga tatttgctaa cgatttagaa ttattagtgc   2940
cggcaattac ctataataag gatattaatt ctaatttatc attcggtgtt gctactgctt   3000
taactcaaaa cggtaatatt aaaggtaatg tagatttcaa taatcaagca gcagtttataa   3060
cacttggtgc aaaataaaaat atcaccgata gtgttacaag taccggcggt gttaacggta   3120
caatcattgc aactggtgca agtattatta atggacctat tacgaatctc gctatgttaa   3180
aagtaggtgc cgggactgta agcataacca aaggcggtaa tactagtatc accgaaatcc   3240
```

```
aaggtaacgg tactgcactc ttaaacatta cctgcaaact ttaacttaac aggcagcata    3300
aataaaaccg gcggtcaggc tctgaagtta aacttcacga atggcggtag tgttagcggt    3360
gttgtaggga ctgcggctaa ttcggttggt gatatcacaa cggcaggcac aacaaacttt    3420
gcaagcagtg ttaatgcaaa aggtgcggcg acgctcggcg atactacaag ttttgccgat    3480
atatttacta acaccggtgc agttacttta gctaaagctt ctatcactaa ttttgctaaa    3540
aacgtaacgg ctaccagctt tgcagctaac aatgctacta ttaatttcgg taatagccta    3600
gcctttaata gtaatataac aggtagcggt actacactta ctttaggtgc aagccaagta    3660
acatataccg gcaccggtag ctttactgat acgctaacct aaatactac ttttgacgga    3720 gcagctaagt caggcggtaa tatcttaatt aaatcaggta gtactcttga tttatcaggg    3780
gtttcaactt tagcacttgt tgttactgct actaattttg acattaataa tataagcccg    3840
gatacaaaat atacgtaat atctgcagaa acggaaggcg gtttaaagcc tactcccgaa    3900
gagaatgtta aataactat taacaatgat aaccgttttg ttgactttac ttttgatgca    3960
tcgactttaa cgttatttgc tgaagatata gctgaagatg ttatagatga agattttgaa    4020
ccaggcggac cgcttgcaaa tatcccgaat gctgcaaata taagaaatc gcttgagtta    4080 atggaagatg ctccaaacgg ttcggatgta cgtcaagctt tcaataattt cggctttatg    4140
acgccgcaac aagaagcaga tgctgtaact caccttatac aagatgttgt aaaacctagc    4200
gatactatag ctgctattaa taatcaagtt atactaagta atatctcaag tagcttaatt    4260
aatctaaatg ctagaatgga tgcaatacag cccggctgcc gtagctgccg gtgatgagga    4320
cagagatgct aagtttggtg catggataag tccgttgtc ggtaatgcaa cgcagaagat    4380
gcgtaacaat ataagcggtt ataagtctga tacaaccggt ggcactatag ttttgacgg    4440 cttagttaac gatgatttag cactcgggct tgcatataca agagccgata ccgatattaa    4500
gctgaaaaat aataagacgg gcgataagaa taaggtagag agtaacatct attccgtata    4560
cggtttatat aatgtacctt atgaaaatct tttcgttgaa gctatagcat cttactcgga    4620
taataggata aaaagcaaat caagacgtgt tattgcaacg gcactagaga ctgtcggcta    4680
tcaaaccgca agcggtaagt ataaatctga agctataca ggtcagttaa tggctggtta    4740
tacctatatg atgcctgaga atattaactt aacaccgctt gcagggctta gatattcggc    4800
tatcaaagat aagggctata aggaaactgg tactactaac caaaaccttta tagttaaagg    4860 caagaactat aatagcttcg atggtttact cgacggtaaa gtatcaagta atatcaatgt    4920
caatgaagaa gtagtgctaa cacctgagct ttacgcaatg gttgattatg cattcaagaa    4980
taaagttccg gcgattgatg caagattaca aggtatgact gctccttac caacagcttt    5040 aagcaaagca aaacaagctt tgatgtcggc gtcggtgtta ctgctaagca caaatgatg    5100 gaatacggta ttaactacga tacaaatatc ggaagtaagt atttcgctca gcaaggtagt    5160 gtaaagttc gtgtaaactt ctaatatact ctagctcgtc attgcgagca gccataggct    5220
gcgtggcaat ctcatgaaat aataacgaac tcctgaggtt gccacgtcaa ggcttcgcct    5280
ttcctcgcaa tgacggaaag ccaaatcacg cagaaatgac atcgaacatc tacaaaaaca    5340
atataaaagc ctatatagtt tgactatata ggcttttttg cttttataatg tagtcttgag    5400 agccgtcatt gcgagcagcc ataggctgcg tggcaatctc gtcaaacatc ttgagattac    5460
cgcgtcgctt cgctcctcgc aatgacgata aaatttaaat aaaaaattat gtt           5513
```

<210> SEQ ID NO 4

```
<211> LENGTH: 30
<212> TYPE: DNA
<213> ORGANISM: Artificial Sequence
<220> FEATURE:
<223> OTHER INFORMATION: Description of Artificial Sequence: primer
      sequence

<400> SEQUENCE: 4
agctcctccc gtatctacca ctgaacctaa                                    30

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: primer
      sequence

<400> SEQUENCE: 5
gtaatacgac tcactatagg gc                                            22

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: primer
      sequence

<400> SEQUENCE: 6
agctcctccc gtatctacca ctgaacctaa                                    30

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: primer
      sequence

<400> SEQUENCE: 7
actatagggc acgcgtggt                                                19

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer
      sequence

<400> SEQUENCE: 8
atggcgaata attctccaaa a                                             21

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: primer
      sequence

<400> SEQUENCE: 9
agtgcagcaa ttcgctcccc ct                                            22

<210> SEQ ID NO 10
<211> LENGTH: 22
```

```
<212> TYPE: DNA
<213> ORGANISM: Artificial Sequence
<220> FEATURE:
<223> OTHER INFORMATION: Description of Artificial Sequence: primer
      sequence

<400> SEQUENCE: 10
aataattttg cagcaggtct tt                                          22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: primer
      sequence

<400> SEQUENCE: 11
tgactcaatg ctccacttta gat                                         23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: primer
      sequence

<400> SEQUENCE: 12
ccagacagat gctgccatta agc                                         23

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: primer
      sequence

<400> SEQUENCE: 13
ttccgatcta gacttcctcc aagc                                        24

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: primer
      sequence

<400> SEQUENCE: 14
aggcggtgat aatgtaggtg tct                                         23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: primer
      sequence

<400> SEQUENCE: 15
ttactcgcag ctccaaaatc tat                                         23

<210> SEQ ID NO 16
<211> LENGTH: 21
<212> TYPE: DNA
```

```
<213> ORGANISM: Artificial Sequence
<220> FEATURE:
<223> OTHER INFORMATION: Description of Artificial Sequence: primer
      sequence

<400> SEQUENCE: 16
gctggaggaa gcctagctgc g                                               21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: primer
      sequence

<400> SEQUENCE: 17
tgaccaaccg aattagccgc                                                 20

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: primer
      sequence

<400> SEQUENCE: 18
ggtggtcagg ctctgaagct aaaac                                           25

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: primer
      sequence

<400> SEQUENCE: 19
tgcagtttga taaccgacag tctc                                            24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: primer
      sequence

<400> SEQUENCE: 20
actggtggca ctataggttt tgac                                            24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: primer
      sequence

<400> SEQUENCE: 21
atcggcagtt tttctaataa taat                                            24
```